US010902954B2

(12) United States Patent
Dias Generoso et al.

(10) Patent No.: US 10,902,954 B2
(45) Date of Patent: Jan. 26, 2021

(54) MOSQUITO POPULATION MINIMIZER

(71) Applicant: INTERNATIONAL BUSINESS MACHINES CORPORATION, Armonk, NY (US)

(72) Inventors: Tiago Dias Generoso, Minas Gerais (BR); Thales Henrique Taveira Garcia, Campinas (BR); Fabrizio Nascimento Caldas, Sumaré (BR); Fabio Minoru Tanada, Campinas (BR)

(73) Assignee: International Business Machines Corporation, Armonk, NY (US)

( * ) Notice: Subject to any disclaimer, the term of this patent is extended or adjusted under 35 U.S.C. 154(b) by 282 days.

(21) Appl. No.: 16/017,323

(22) Filed: Jun. 25, 2018

(65) Prior Publication Data

US 2019/0392954 A1    Dec. 26, 2019

(51) Int. Cl.
*G16H 50/80* (2018.01)
*G06Q 30/02* (2012.01)
*G16H 50/30* (2018.01)
*G06F 16/29* (2019.01)

(52) U.S. Cl.
CPC ......... *G16H 50/80* (2018.01); *G06Q 30/0269* (2013.01); *G16H 50/30* (2018.01); *G06F 16/29* (2019.01)

(58) Field of Classification Search
CPC .......... G06Q 10/0635; G06Q 10/0637; G16H 50/30; G16H 50/80; G06F 16/29
See application file for complete search history.

(56) References Cited

U.S. PATENT DOCUMENTS

| 4,937,555 A | 6/1990 | Litzkow et al. |
| 7,155,423 B1 * | 12/2006 | Josephson ............. G06Q 10/06 706/60 |

(Continued)

FOREIGN PATENT DOCUMENTS

| CN | 102897323 A | 1/2013 |
| WO | WO2010062256 A1 | 6/2010 |
| WO | WO2016064735 A1 | 4/2016 |

OTHER PUBLICATIONS

Moussavi, Massoud et al., Decision Support Tools for Malaria Prevention and Treatment USAID, Nov. 2017 (Year: 2017).*

(Continued)

*Primary Examiner* — Scott L Jarrett
(74) *Attorney, Agent, or Firm* — Patrick J. Daugherty; Daugherty & Del Zoppo Co. LPA

(57) ABSTRACT

Aspects automatically identify and minimize local populations of mosquitoes wherein processors are configured to assign different exposure risk values to different geographic locations as a function of determining different respective values of likelihood that each of the locations will experience a threshold exposure to mosquito activity, assign population risk values to the locations as a function of population data, filter a location from the plurality of locations to generate a filtered remainder set of the locations as a function of one or more one risk values of the exposure risk value and the population risk value failing to meet a minimum threshold value, rank the filtered remainder set of the geographic locations, and associate each of a plurality of mosquito activity abatement actions to each of the ranked filtered remainder set of the geographic locations.

20 Claims, 4 Drawing Sheets

(56) References Cited

U.S. PATENT DOCUMENTS

| | | | |
|---|---|---|---|
| 8,400,348 B1 | 3/2013 | Guice et al. | |
| 8,614,633 B1* | 12/2013 | Lear | G08B 29/188 |
| | | | 114/382 |
| 9,058,354 B2* | 6/2015 | Dolan | G06Q 50/22 |
| 9,746,985 B1* | 8/2017 | Humayun | G06Q 10/10 |
| 2001/0027388 A1* | 10/2001 | Beverina | G06Q 20/206 |
| | | | 703/22 |
| 2004/0103058 A1* | 5/2004 | Hamilton | G06Q 10/10 |
| | | | 705/38 |
| 2005/0060213 A1* | 3/2005 | Lavu | G06Q 30/0283 |
| | | | 705/1.1 |
| 2008/0140431 A1* | 6/2008 | Anderson | A01B 79/005 |
| | | | 701/50 |
| 2009/0216860 A1 | 8/2009 | Li et al. | |
| 2012/0005115 A1* | 1/2012 | Hofberg | G06Q 10/067 |
| | | | 705/348 |
| 2012/0035958 A1* | 2/2012 | Rhine-Pallas | G06F 19/3456 |
| | | | 705/3 |
| 2012/0210644 A1* | 8/2012 | Johnson | G06N 5/02 |
| | | | 47/1.01 R |
| 2013/0197965 A1* | 8/2013 | Leitch | G06Q 10/0635 |
| | | | 705/7.28 |
| 2015/0186602 A1* | 7/2015 | Pipke | A61B 5/7275 |
| | | | 705/3 |
| 2016/0232621 A1* | 8/2016 | Ethington | G06Q 50/02 |
| 2016/0253595 A1* | 9/2016 | Mathur | G06N 7/005 |
| | | | 706/12 |
| 2018/0150601 A1* | 5/2018 | Astigarraga | G06Q 50/01 |
| 2019/0096526 A1* | 3/2019 | Hirsch | G16H 50/70 |
| 2019/0148023 A1* | 5/2019 | Sadilek | G16H 50/80 |
| | | | 705/2 |

OTHER PUBLICATIONS

Chanda, Emmanuel et al., Using a Geographical-Information-System-Based Decision Support to Enhance Malaria Vector Control in Zambia, Journal of Tropical Medicine, vol. 12, 2012 (Year: 2012).*

Lozano, Saul et al., Chapter 6: Emerging Information Technologies to Provide Improved Decision Support for Surveillance, Prevention, and Control of Vector Borne Diseases; Efficient Decision Support Systems—Practice and Challenges in Biomedical Related Domain, pp. 89-114, Sep. 2011 (Year: 2011).*

Rakotomana, Fanjasoa et al., Determining areas that require indoor insecticide spraying using Multi Criteria Evaluation, a decision support tool malaria vector control programmes in the Central Highlands of Madagascar, International Journal of Health Geographics, Jan. 2007 (Year: 2007).*

Hongoh, Valerie et al., Assessing Interventions to Manage West Nile Virus Using Multi-Criteria Decision Analysis with Risk Scenarios,PLos One, vol. 11, No. 8, 2016 (Year: 2016).*

Eiras, Alvaro Eduardo et al., Preliminary Evaluation of the "Dengue-MI" Cad. Saude Publicao, Sep. 25, 2009 (Year: 2009).*

Pepin, Kim M., Utility of mosquito surveillance data for spatial prioritization of vector control against denuge viruses in three Brazilian cities, Parasites & Vectors, 2015 (Year: 2015).*

Barker, CM, et al., Decision Support System for Mosquito and Arbovirus Control in California Oceanic Engineering Society, Sep. 24, 2010 (Year: 2010).*

Wangdi, Kinley et al., Development and evaluation of a spatial decision support system for malaria elimination in Bhutan Malaria Journal, vol. 15, 2016 (Year: 2016).*

Morgan D. et al., Assessing the risk from emerging infections Epidemiol. Infect. vol. 137, 2009 (Year: 2009).*

Michel, Pascal, Prioritization tools for diseases and interventions targeting populations in Africa and Canada vulnerable to water-related health issues, Jun. 2016 (Year: 2016).*

Hongoh, Valerie et al., Spatially explicit multi-criteria decision analysis fo rmanaging vector-borne diseases International Journal of Geographics, vol. 10, 2011 (Year: 2011).*

Peter Mell et al, The NIST Definition of Cloud Computing, National Institute of Standards and Technology, Publication 800-145, 2011, entire document.

Jephtha C. Ninor et al, Topographic models for predicting malaria vector breeding habitats: potential tools for vector control managers, Parasites & Vectors, 2013, entire document.

Andy Hardy et al, Using low-cost drones to map malaria vector habitats, Parasites & Vectors, 2017, entire documenty.

* cited by examiner

MOSQUITO POPULATION MINIMIZER

BACKGROUND

Several diseases like Yellow Fever, Dengue, Zika, and Chikungunya are transmitted by *Aedes Aegypti*, a common mosquito species. In order to prevent the *Aedes Aegypti* population from growing, health officials target *Aedes Aegypti* areas of concern like vacant pools and other areas of standing water. Health officials generally rely on local populations to identify such areas of concern. For example, if a given area has a high incidence of *Aedes Aegypti* spread diseases, a member of the population, for example a local doctor, must first inform the proper health officials of the high incidence before any preventative measures can be taken. In other situations, the local health officials may have access to databases containing public health data like disease incidence data acquired from a local hospital, historical data of disease incidence for a given area, or social media complaints regarding the outbreak of *Aedes Aegypti* carried diseases.

After the local population has identified a potential area of concern and notified the proper health officials, then a health official can visit the identified potential area of concern to manually inspect the site. If the health official determines the location is an *Aedes Aegypti* area of concern, then proper action can be taken in order to eradicate the area of concern.

SUMMARY

In one aspect of the present invention, a computerized method for automatically identifying and minimizing localized populations of mosquitoes includes executing steps on a computer processor. Thus, a computer processor is configured to assign different exposure risk values to each of a plurality of different geographic locations of interest as a function of determining different respective values of likelihood that each of the locations of interest will experience a threshold exposure to mosquito activity as a function of correlations of weather condition information for each of the locations of interest to mosquito activity data within each of the different geographic locations of interest, assign population risk values to each the locations of interest as a function of respective population data for each of the locations of interest, filter a first location of interest from the plurality of locations of interest to generate a filtered remainder set of the locations as a function of a selected (one or more) risk value of the exposure risk value and the population risk value failing to meet a minimum threshold value, rank the filtered remainder set of the geographic locations of interest as a function of their respective exposure risk values and population risk values, and associate each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations.

In another aspect, a system has a hardware processor in circuit communication with a computer readable memory and a computer-readable storage medium having program instructions stored thereon. The processor executes the program instructions stored on the computer-readable storage medium via the computer readable memory and is thereby configured to assign different exposure risk values to each of a plurality of different geographic locations of interest as a function of determining different respective values of likelihood that each of the locations of interest will experience a threshold exposure to mosquito activity as a function of correlations of weather condition information for each of the locations of interest to mosquito activity data within each of the different geographic locations of interest, assign population risk values to each of the locations of interest as a function of respective population data for each of the locations of interest, filter a first location of interest from the plurality of locations of interest to generate a filtered remainder set of the locations as a function of a selected (one or more) risk value of the exposure risk value and the population risk value failing to meet a minimum threshold value, rank the filtered remainder set of the geographic locations of interest as a function of their respective exposure risk values and population risk values, and associate each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations.

In another aspect, a computer program product for automatically identifying and minimizing localized populations of mosquitoes includes executing steps on a computer processor that has a computer-readable storage medium with computer readable program code embodied therewith. The computer readable hardware medium is not a transitory signal per se. The computer readable program code includes instructions for execution which cause the processor to assign different exposure risk values to each of a plurality of different geographic locations of interest as a function of determining different respective values of likelihood that each of the locations of interest will experience a threshold exposure to mosquito activity as a function of correlations of weather condition information for each of the locations of interest to mosquito activity data within each of the different geographic locations of interest, assign population risk values to each the locations of interest as a function of respective population data for each of the locations of interest, filter a first location of interest from the plurality of locations of interest to generate a filtered remainder set of the locations as a function of a selected (one or more) risk value of the exposure risk value and the population risk value failing to meet a minimum threshold value, rank the filtered remainder set of the geographic locations of interest as a function of their respective exposure risk values and population risk values, and associate each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations.

BRIEF DESCRIPTION OF THE DRAWINGS

These and other features of embodiments of the present invention will be more readily understood from the following detailed description of the various aspects of the invention taken in conjunction with the accompanying drawings in which.

DETAILED DESCRIPTION

Figure 1:
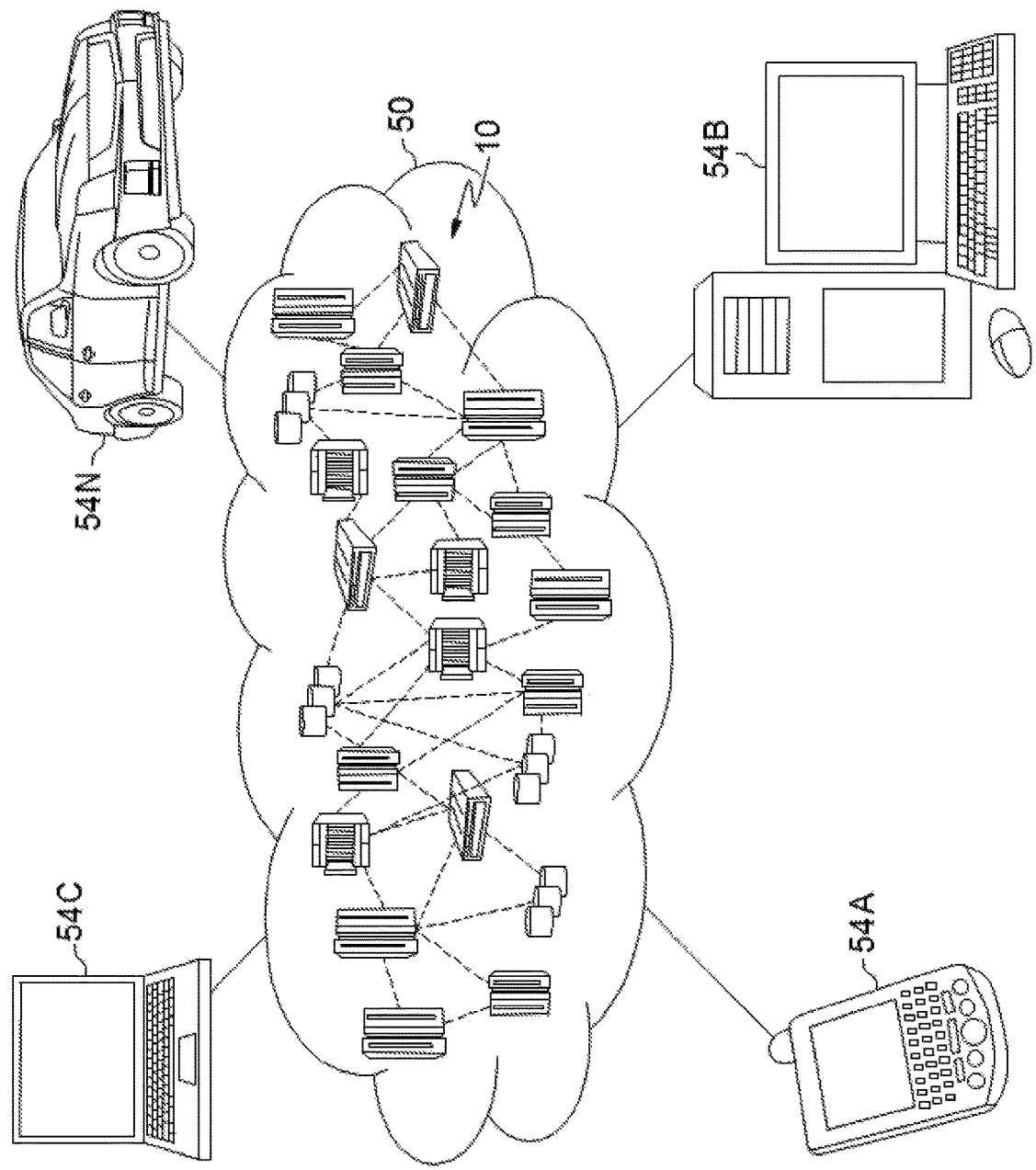
FIG. 1 depicts a cloud computing environment according to an embodiment of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, mechanically encoded devices such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with an area of concern on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
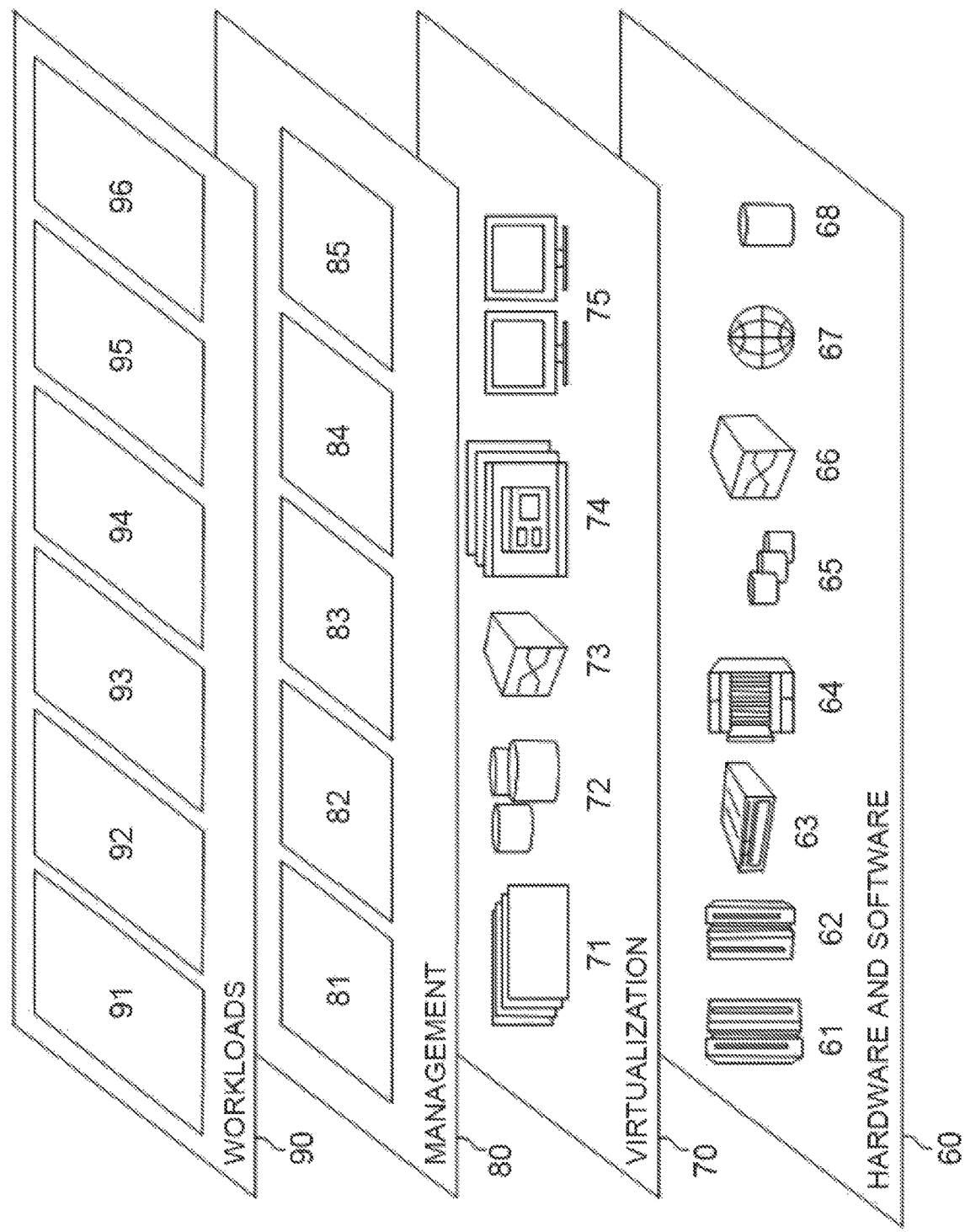
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing for automatically identifying and minimizing *Aedes Aegypti* mosquito areas of concern 96.

Figure 3:
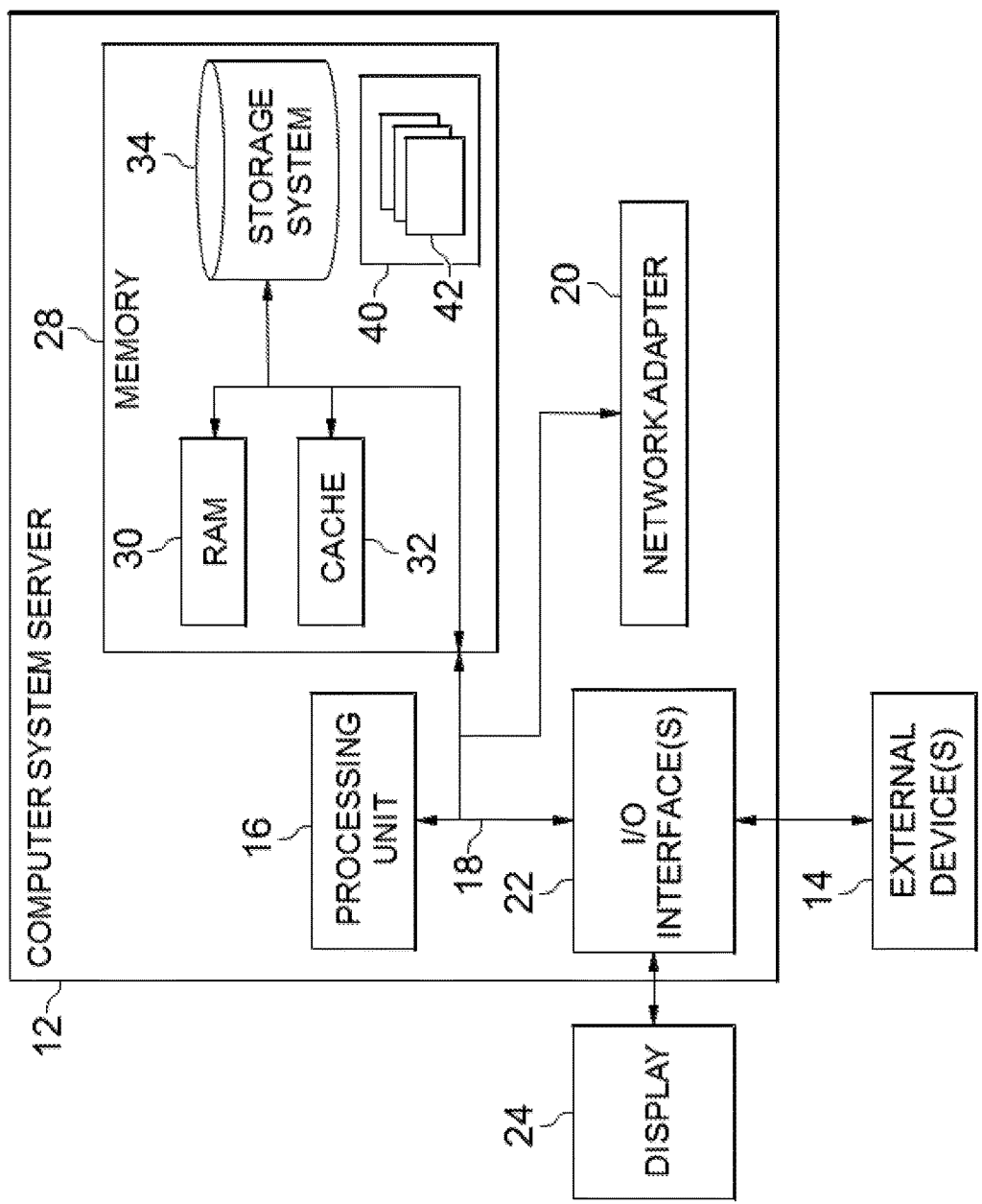
FIG. 3 depicts a computerized aspect according to an embodiment of the present invention.

FIG. 3 is a schematic of an example of a programmable device implementation 10 according to an aspect of the present invention, which may function as a cloud computing node within the cloud computing environment of FIG. 2. Programmable device implementation 10 is only one example of a suitable implementation and is not intended to suggest any limitation as to the scope of use or functionality of embodiments of the invention described herein. Regardless, programmable device implementation 10 is capable of being implemented and/or performing any of the functionality set forth hereinabove.

A computer system/server 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

The computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating systems, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 4:
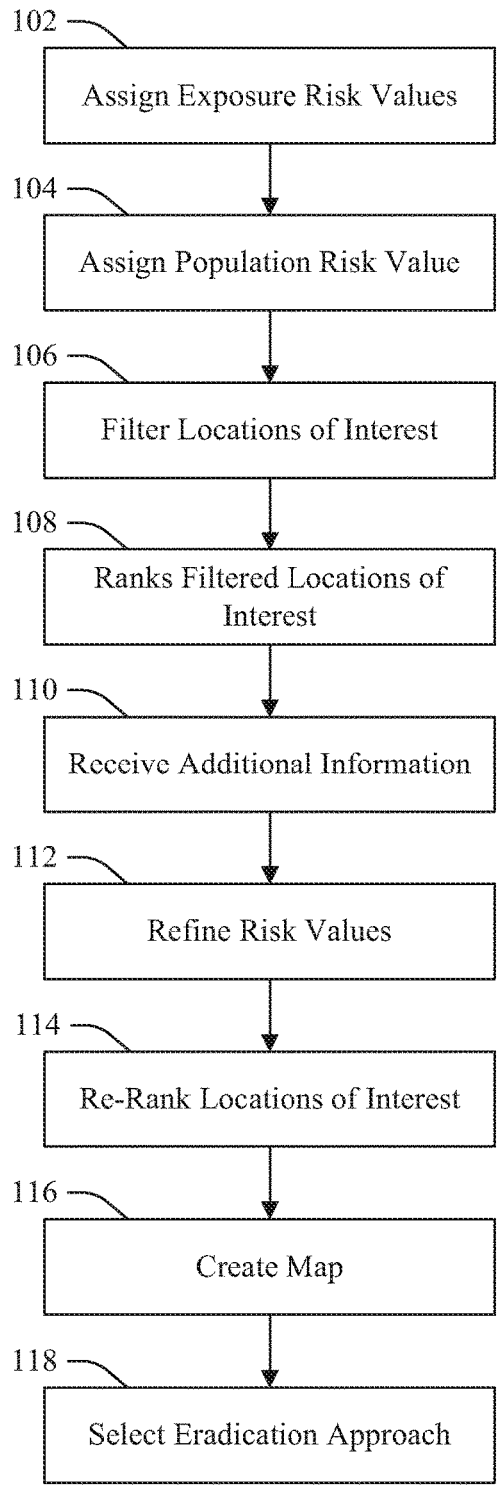
FIG. 4 is a flow chart illustration of an embodiment of the present invention.

FIG. 4 illustrates a process or system according to the present invention for automatically identifying and minimizing *Aedes Aegypti* or other mosquito areas of concern.

At 102, a processor that is configured according to an aspect of the present invention (the "configured processor") assigns different exposure risk values to each of a plurality of different geographic locations of interest as a function of determining different respective values of likelihood that each of the locations of interest will experience a threshold exposure to mosquito activity as a function of correlations of weather condition information for each of the locations of interest to mosquito activity data within each of the different geographic locations of interest.

The configured processor defines the locations by address; regional designation (neighborhood, city, town, county state, etc.); Global Positioning System (GPS) (coordinate boundaries or ranges, etc.) In one instance, a location of interest is identified as a function of data submitted by a user. For example, a user may complain of a large number of mosquitoes within their (first) community during a current weather or climate condition (average or range of ambient temperatures, humidity, dew point, total inches/millimeters of rainfall experienced over the past 72 hours, etc.). The configured processor determines that this community is more likely to experience threshold exposures to mosquito activity than a different (second), neighboring community that has similar demographic data or geographic characteristics as a function of determining lower reported levels of mosquito activity for the neighboring community during similar weather conditions in historic data. Thus, even though both communities should be expected to report the same levels during the same conditions from prior art projection models, the configured processor labels the first community with a higher ranking value as a function of determining that it will likely experience higher levels in the future during the same conditions. In another example, in response to an input of a report from a local physician of a high (or threshold) number of individuals from the first community with diseases usually carried by *Aedes Aegypti*, the configured processor responsively labels this area (at 102) as more likely to experience threshold exposures to mosquito activity than another area having lower (or less than threshold) amounts of the reported diseases during similar weather conditions.

In another instance, the configured processor assigns exposure risk values for locations of interest in response to processing governmental records and databases. For example, the configured processor may search a disease location index corresponding to diseases usually carried by *Aedes Aegypti* to identify a location of interest as one that has a threshold number of the diseases or a threshold positive rate-of-change in reported incidents, over a specified timeframe, and responsively label the area for preventive measures prior to a predicted weather condition known to increase levels of mosquito activity.

In another example, the configured processor may search census records to identify likely locations of interest as a function of threshold levels of at-risk populations. For example, in response to determining that a percentage of people between age 75 to 80 (that heath data indicates are more susceptible to mosquito-borne illnesses) within a given area exceeds a predetermined threshold, the configured processor identifies (ranks more highly) the area as a location of interest, to be prioritized over another area having similar general population densities, climate and topography, etc.

In yet another example, the configured processor may search local atlas databases for known locations of standing water (illustrative but not limiting examples include active construction sites, dumping locations, lakes, lagoons, and pools), which the configured processor then identifies as locations of interest relative to other regions having similar general population densities, climate and topography, etc.

In yet another instance, the configured processor ranks or identifies the location of interest by analyzing image data for relative amounts or percentages of standing water. The image data includes photographs or video supplied by a drone flown over a location. The configured processor may receive and process the recording in real time, or process historic image data at a later time. The configured processor may analyze image data with visual recognition application program interfaces in order to identify areas of standing water, to identify locations with an amount of standing water that exceeds a predetermined threshold as the location of interest. For example, the predetermined threshold may be a percentage (10%, 20%, 30%, etc.) of a total area of the recording occupied by standing water that is within an exposure proximity distance to populated areas within the location of interest.

More particularly, the configured processor assigns an exposure risk value to the locations of interest at 102 as a function of obtained or predicted weather condition information (illustrative but not limiting examples include rainfall index, temperature, and humidity) for the locations of interest or other information that indicates an area of interest is at an increased risk of exposure to *Aedes Aegypti* (illustrative but not limiting examples include the amount of standing water within a location of interest or the known population of *Aedes Aegypti* within a location of interest).

A user may supply the weather information, or the configure processor may search weather databases for the weather information. The weather information includes but is not limited to humidity and predicted rain over a predetermined minimum amount of time as a function of a surface area amount of impermeable surfaces known to generate pools of standing water (for example, concrete, asphalt, clay, etc.) within the location of interest that is related to the life span of *Aedes Aegypti* or the amount of time needed for *Aedes Aegypti* gestation. The configured processor may assign a higher value for a location of interest with weather patterns more susceptible to inducing *Aedes Aegypti* areas of concern (illustrative but not limiting examples include higher amounts of rainfall and average humidify within a location of interest and during a time period of temperatures within a predetermined temperature, humidity and/or dew-point range required for *Aedes Aegypti* gestation or vitality).

At 104, the configured processor assigns a population risk value to the location of interest as a function of population data. Illustrative but not limiting or exhaustive examples of population data considered include census or other population records for a given region, and number of healthcare facilities within or proximate to the location of interest. For example, the configured processor assigns a greater value to a location of interest with a higher population than one assigned to a location of interest with a smaller population. In another example, the configured processor assigns a higher value to a location of interest farther from a healthcare facility than another location of interest that is closer to a healthcare facility.

At 106, the configured processor filters out locations of interest as a function of one or both of the exposure risk and population risk values failing to meet a minimum threshold value to generate a filtered remainder set of the geographic locations; for example, an amount of surface area holding standing water determined within a location of interest failing to meet a minimum exposure risk threshold value of surface area. Thus, in response to determining that a location of interest has an exposure risk value or population risk value that is less than a predetermined threshold, the configured processor removes the location of interest from consideration for abatement measures (as described below). In another example, in response to determining that a ranked location of interest is likely to have an amount of standing water that is less than a predetermined threshold regardless of current or future weather conditions, the configured processor removes the location of interest from consideration (thus, in response to determining that the level of potential risk form mosquito exposure does not present a minimum level of risk justifying mosquito abatement costs).

At 108, the configured processor ranks the remaining (filtered) location of interests relative to each other for priority for deploying mosquito abatement measures as a function of the values of their respective exposure risk and population risk values. For example, the configured processor ranks a first location of interest with a higher combined value (summed, multiplied result, etc.) of exposure risk and population risk values ahead of another location of interest with a lower combined value. The exposure risk and population risk values may also be differentially weighted (based on the relative strength of correlation to increased mosquito population or levels, etc.), so that one is more dispositive of the generated abatement priority ranking values than the other.

At 110, the configured processor receives additional information for the locations of interest. In one instance, the additional information includes drone image data for locations of interest previously lacking from consideration in setting the exposure risk or population risk values. The configured processor may then analyze the image data to identify areas of standing water as previously described herein. In another instance, the additional information includes data from a health official that was previously missing. For example, a health official may input an *Aedes Aegypti* disease incidence rate for a location of interest.

At 112, the configured processor weights, revises, learns or refines the exposure risk or population risk values as a function of the additional information. For example, if the configured processor determines there is a higher amount of standing water for a location of interest from the additional information, or a data input or revision identifies a location of interest as having a higher reported or predicted *Aedes Aegypti* population than previously determined or ranked, then the configured processor may increase the exposure risk value.

At 114, the configured processor re-ranks the locations of interest as a function of the refined/weighted exposure risk or population risk values.

At 116, the configured processor generates a map output to a graphical user interface (GUI) that visually indicates and distinguishes the locations of interest as a function of their respective ranking values. For example, a location of interest with a higher rank may be marked red while a location of interest with a lower rank may be marked in green.

At 118, the configured processor selects for deployment (associates) each of a plurality of different mosquito activity abatement actions to each of the ranked filtered set of the geographic locations in order of their respective rankings as a function of matching respective deployment cost values of the mosquito activity abatement actions to respective exposure risk weighting and population risk weighting values of the rank locations.

In some embodiments, the total number of abatement actions, or total budget for abatement costs of all actions is limited to a maximum value, wherein the association of abatement actions at 118 allocates the actions to the locations in order of their rankings until the maximum value is met, so that the lowest-ranked location my not receive abatement actions, or only low-cost abatement actions.

Illustrative but not limiting examples of abatement actions include eliminating standing water, spraying insecticides within the locations, fining property owners for failure to abate standing water hazards, etc. For example, the configured processor may recommend a more costly eradication action for a more densely populated location of interest (one having a higher exposure risk or population risk value) than another location of interest with a lower corresponding value, and thus, in response to determining that the differences in rank and/or population values for the more-populous location of interest is an indication of a need for a more aggressive, and costly, eradication approach.

Figure 5:
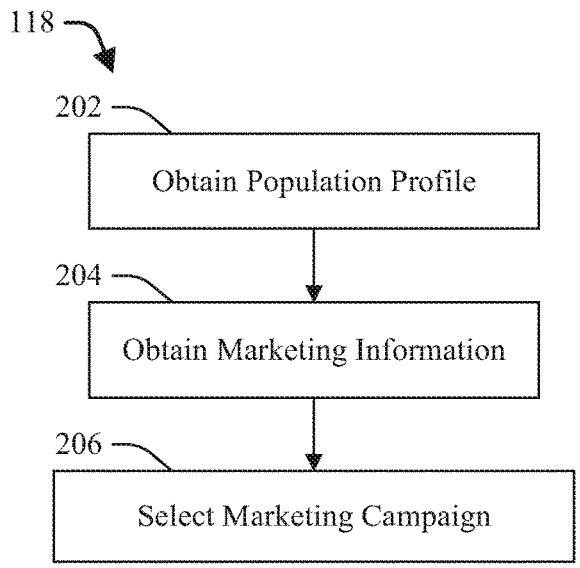
FIG. 5 is another flow chart illustration of an embodiment of the present invention.

FIG. 5 illustrates another embodiment according to the present invention that selects and deploys *Aedes Aegypti* mosquito eradication or hazard abatement actions to areas of concern (at 118 of FIG. 4) as a function determining respective costs of deployment of the selected actions from marketing and demographic data.

At 202, the configured processor determines an age band value for a ranked location of interest. The age band value includes a number of people that fall within a band of predetermined ages, illustrative but not limiting examples include 20-25, 26-30, or 31-35. In another instance, the configured processor determines the bands of predetermined ages as a function of a median or average age of a ranked location of interest and a number of standard deviations. For example, if the configured processor determines that the median age of a ranked location of interest is 40 and that one standard deviation above the median age is 55 and one standard deviation below the median age is 25, then the configured processor may determine the range of predetermined ages as between 25-40 and 41-55.

The configured processor determines the age band value from a census data, including via a statistical analysis of the age data for a population or bands or distinct populations within a ranked location of interest. For example, the configured processor may determine 2,000 people fall between the ages of 20-25 and 3,000 people fall between the ages of 50-55 for a ranked location of interest. As a result, the predetermined processor determines the age band value for the ranked location of interest as 50-55. In another instance, the configured processor ranks age bands as a function of the number of people that fall between the predetermined age ranges. For example, if the configured processor determines 1,000 people fall between 18-25, 750 people fall between 26-30, and 1,100 people fall between 31-35, the configured processor ranks the 31-35 age band as first, the 18-25 age band as second, and the 26-30 age band as third for a ranked location if interest.

At 204, the configured processor determines marketing information that most effectively reaches the predetermined age bands. The configured processor may search databases for marketing information data and therefrom determine which forms of media (illustrative but not limiting examples include public addresses, local media campaigns, social media ads, direct mailing ads, radio ads, and television ads) most effectively reach different age bands. For example, the configured processor may obtain marketing information from a known database that indicates young adults ages 18-24, which corresponds to one age band value, are more likely to see a social media ad than older adults ages 65 and older, which corresponds to another age profile value. In another example, the configured processor may obtain marketing information from a known database that indicates adults ages 30-35 are more likely to hear a radio ad than see a television ad.

At 206, the configured processor determines or selects a marketing campaign as a function of matching the determined age band value to most appropriate or cost-efficient marketing information. The marketing campaign may include pertinent information from health officials indicating that the location of interest is a high risk area for the *Aedes Aegypti* carried diseases and recommendations for preventing the spread of *Aedes Aegypti*. For example, if at 202 the configured processor determines the age band value to be 20-25, the marketing information indicates that the most effective form of marketing to reach people between 20-25 is a television ad, then the configured processor determines a television ad as the marketing campaign. In another instance, the configured processor determines the marketing campaign as a function of total cost of the campaign as well as a predetermined amount of funding allocated to the marketing campaign. For example, the configured processor may determine that the most effective form of marketing for a given age band is a television ad, but the amount of funding allocated to the campaign could afford only eight television ads and further determines that 10 television ads are needed in order to effectively reach the age band, and further determines that the next most effective campaign is a newspaper ad campaign that is fully affordable and more effective than the eight television ads, then the configured processor determines that the marketing campaign is a newspaper ad campaign.

In another instance, the configured processor further determines a timing of ads needed to most effectively reach the determined age band. For instance, if the configured processor determines the marketing campaign as a television ad campaign, the configured processor may further determine the most effective time to reach a given age band as a function of a number of number of television viewers within the determined age band. For example, if the highest number of viewers within the determined age band is 7:00 P.M. on Wednesday, then the configured processor determines the marketing campaign as a television ad campaign that will run at 7:00 P.M. on Tuesday.

In yet another instance, the configured processor further determines the marketing campaign as a function of the exposure risk weighting of the location of interest and a cost of the marketing campaign. For example, if one location of interest has a higher risk weighting, then the configured processor may allocate more funding of a total available funding to a marketing campaign for that location of interest than a location of interest with a lower risk weighting.

Control and reduction of health exposure risks presented by populations of *Aedes Aegypti* can be very difficult under prior art processes. Targeting *Aedes Aegypti* areas of concern like vacant pools and other areas of standing water is difficult as health officials often do not know where the areas of concern are located. As a result, health officials generally rely on self-reporting by local populations to identify areas of concern. For example, if a given area has a high incidence of *Aedes Aegypti* spread diseases, a member of the population, for example a local doctor, must first inform the proper health officials of the high incidence before any preventative measures can be taken. In other situations, the local health officials may have access to databases containing public health data like disease incidence data acquired from a local hospital, historical data of disease incidence for a given area, or social media complaints regarding the outbreak of *Aedes Aegypti* carried diseases. Even with access to these databases, a health official is still needed to actively review them and make discretionary determinations under the prior art. Moreover, after the local population has identified a potential area of concern and notified the proper health officials, a health official must visit the identified potential area of concern to manually inspect the site under the prior art, wherein if the health official determines the location is an *Aedes Aegypti* area of concern, the health official takes steps to initiate one or more abatement actions in order to eradicate problems within the area of concern. Such prior art manual inspection processes are inefficient, costly with respect to manpower, and place a strain on the local health officials as this process is time and labor intensive.

In contrast, embodiments of the present invention automatically identify and rank discrete areas of concern for potential *Aedes Aegypti* exposures as a function of values determined from multiple, unrelated characteristics inclusive of population densities and demographics, health and medical services capacities, climate, topography, etc., in a multi-factor process that autonomously identifies, selects and implements appropriate abatement actions, matching the highest-cost and most effective implementations to the highest weighted locations of interest, and thus, lower cost implementations to other locations having lower weightings.

The terminology used herein is for describing particular aspects only and is not intended to be limiting of the invention. As used herein, the singular forms "a", "an" and "the" are intended to include the plural forms as well, unless the context clearly indicates otherwise. It will be further understood that the terms "include" and "including" when used in this specification specify the presence of stated features, integers, steps, operations, elements, and/or components, but do not preclude the presence or addition of one or more other features, integers, steps, operations, elements, components, and/or groups thereof. Certain examples and elements described in the present specification, including in the claims, and as illustrated in the figures, may be distinguished, or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations, or process steps.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising executing on a computer processor:
   a computerized device analyzing via execution of a visual recognition application program image data of a plurality of different geographic locations to determine respective percentages of standing water within surface areas of each of the geographic locations occurring during a weather condition over a time period, wherein the weather condition is at least one of an ambient temperature value, a humidity value, a dew point value, and a rainfall amount value;
   correlating reported levels of mosquito activity within each of the different geographic locations to the weather condition;
   the computerized device determining different exposure risk values for the weather condition for each of the plurality of different geographic locations of interest as a function of the respective determined percentages of standing water and the correlated reported levels of mosquito activity;
   the computerized device determining population risk values for each of the locations of interest in proportion to respective population data values for each of the locations of interest;
   filtering a first location of interest from the plurality of locations of interest to generate a filtered remainder set of the locations as a function of at least one risk value selected from the group consisting of the exposure risk value and the population risk value of the first location failing to meet a minimum threshold value;
   ranking the filtered remainder set of the geographic locations of interest as a function of their respective exposure risk values and population risk values; and
   the computerized device autonomously identifying, selecting and implementing each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations, wherein the mosquito activity abatement actions are at least one of eliminating standing water within the geographic locations and spraying insecticides within the geographic locations.

2. The method of claim 1, wherein the plurality of mosquito activity abatement actions has a total budget cost; and
   wherein the of autonomously identifying, selecting and implementing each of the plurality of mosquito activity abatement actions to each of the ranked filtered remainder set of the geographic locations allocates the actions to the locations in order of their rankings until a maximum value is met.

3. The method of claim 1, further comprising:
   analyzing the image data to determine respective surface area amounts of impermeable surfaces within the locations of interest and
   determining the respective percentages of standing water within the surface areas as a function of the determined respective surface area amounts of impermeable surfaces.

4. The method of claim 1, wherein the exposure risk values are assigned as a function of respective amounts of mosquito carried diseases within the geographic locations of interest.

5. The method of claim 1, further comprising:
   determining the population risk values in proportion to respective numbers of healthcare facilities within each of the geographic locations of interest.

6. The method of claim 1, further comprising:
   determining population profile data for a highest-ranked location of the ranked filtered remainder set of the geographic locations;
   determining marketing information deployment costs for each of the mosquito activity abatement actions that are associated to the highest-ranked location as a function of the determined population profile data; and
   selecting a marketing campaign of the mosquito activity abatement actions that are associated to the highest-ranked location in response to determining that the selected marketing campaign best matches the determined population profile data at a deployment cost that meets a threshold associated with the exposure risk weighting and the population risk weighting values of the highest-ranked location.

7. The method of claim 1, further comprising:
   integrating computer-readable program code into a computer system comprising a processor, a computer readable memory in circuit communication with the processor, and a computer readable storage medium in circuit communication with the processor; and
   wherein the processor executes program code instructions stored on the computer-readable storage medium via the computer readable memory and thereby performs the analyzing the image data to determine the respective percentages of standing water, the correlating the reported levels of mosquito activity, the determining the different exposure risk values, the determining population risk values, the filtering the first location of interest, the ranking the filtered remainder set, and the identifying, selecting and implementing each of the plurality of mosquito activity abatement actions.

8. The method of claim 7, wherein the computer-readable program code is provided as a service in a cloud environment.

9. A system comprising:
   a processor;
   a computer readable memory in circuit communication with the processor; and
   a computer readable storage medium in circuit communication with the processor;
   wherein the processor executes program instructions stored on the computer-readable storage medium via the computer readable memory and thereby:
   analyzes via execution of a visual recognition application image data of a plurality of different geographic locations to determine respective percentages of standing water within surface areas of each of the geographic locations occurring during a weather condition over a time period, wherein the weather condition is at least one of an ambient temperature value, a humidity value, a dew point value, and a rainfall amount value;
correlates reported levels of mosquito activity within each of the different geographic locations to the weather condition;
determines different exposure risk values to for the weather condition for each of the plurality of different geographic locations of interest as a function of the respective determined percentages of standing water and the correlated reported levels of mosquito activity;
determines population risk values for each of the locations of interest in proportion to of respective population data for each of the locations of interest;
filters a first location of interest from the plurality of locations of interest to generate a filtered remainder set of the locations as a function of at least risk value selected from the group consisting of the exposure risk value and the population risk value of the first location failing to meet a minimum threshold value;
ranks the filtered remainder set of the geographic locations of interest as a function of their respective exposure risk values and population risk values; and
autonomously identifies, selects and implements each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations, wherein the mosquito activity abatement actions are at least one of eliminating standing water within the geographic locations and spraying insecticides within the geographic locations.

10. The system of claim 9, wherein the plurality of mosquito activity abatement actions has a total budget cost; and
wherein the processor executes program instructions stored on the computer-readable storage medium via the computer readable memory and thereby autonomously identifies, selects and implements each of the plurality of mosquito activity abatement actions to each of the ranked filtered remainder set of the geographic locations allocates the actions to the locations in order of their rankings until a maximum value is met.

11. The system of claim 9, wherein the processor executes program instructions stored on the computer-readable storage medium via the computer readable memory and thereby:
analyzes the image data to determine respective surface area amounts of impermeable surfaces within the locations of interest and
determines the respective percentages of standing water within the surface areas as a function of the determined respective surface area amounts of impermeable surfaces.

12. The system of claim 9, wherein the exposure risk values are assigned as a function of respective amounts of mosquito carried diseases within the geographic locations of interest.

13. The system of claim 9, wherein the processor executes program instructions stored on the computer-readable storage medium via the computer readable memory and thereby:
determines the population risk values in proportion to respective numbers of healthcare facilities within each of the geographic locations of interest.

14. The system of claim 9, wherein the processor executes the program instructions stored on the computer-readable storage medium via the computer readable memory and thereby
determines population profile data for a highest-ranked location of the ranked filtered remainder set of the geographic locations
determines marketing information deployment costs for each of the mosquito activity abatement actions that are associated to the highest-ranked location as a function of the determined population profile data; and
selects a marketing campaign of the mosquito activity abatement actions that are associated to the highest-ranked location in response to determining that the selected marketing campaign best matches the determined population profile data at a deployment cost that meets a threshold associated with the exposure risk weighting and the population risk weighting values of the highest-ranked location.

15. A computer program product comprising:
a computer readable storage medium having computer readable program code embodied therewith, wherein the computer readable storage medium is not a transitory signal per se, the computer readable program code comprising instructions for execution by a processor that cause the processor to:
analyze via execution of a visual recognition application image data of a plurality of different geographic locations to determine respective percentages of standing water within surface areas of each of the geographic locations occurring during a weather condition over a time period, wherein the weather condition is at least one of an ambient temperature value, a humidity value, a dew point value, and a rainfall amount value;
correlate reported levels of mosquito activity within each of the different geographic locations to the weather condition;
determine different exposure risk values for the weather condition for each of the plurality of different geographic locations of interest as a function of the respective determined percentages of standing water and the correlated reported levels of mosquito activity;
determine population risk values for each of the locations of interest in proportion to respective population data for each of the locations of interest;
filter a first location of interest from the plurality of locations of interest to generate a filtered remainder set of the locations as a function of at least one risk value selected from the group consisting of the exposure risk value and the population risk value of the first location failing to meet a minimum threshold value;
rank the filtered remainder set of the geographic locations of interest as a function of their respective exposure risk values and population risk values; and
autonomously identify, select and implement each of a plurality of mosquito activity abatement actions to each of the ranked filtered remainder set of the geographic locations in order of their respective rankings as a function of matching respective deployment cost values of the mosquito activity abatement actions to respective exposure risk weighting and population risk weighting values of the rank locations, wherein the mosquito activity abatement actions are at least one of eliminating standing water within the geographic locations and spraying insecticides within the geographic locations.

16. The computer program product of claim 15, wherein the plurality of mosquito activity abatement actions has a total budget cost; and wherein the computer readable program code instructions for execution by the processor further cause the processor to autonomously identify, select and implement each of the plurality of mosquito activity abatement actions to each of the ranked filtered remainder set of the geographic locations allocates the actions to the locations in order of their rankings until a maximum value is met.

17. The computer program product of claim 15, the computer readable program code instructions for execution by the processor further cause the processor to:

analyze the image data to determine respective surface area amounts of impermeable surfaces within the locations of interest and determine the respective percentages of standing water within the surface areas as a function of the determined respective surface area amounts of impermeable surfaces.

18. The computer program product of claim 15, wherein the exposure risk values are assigned as a function of respective amounts of mosquito carried diseases within the geographic locations of interest.

19. The computer program product of claim 15, wherein the computer readable program code instructions for execution by the processor further cause the processor to:

determine the population risk values in proportion to respective numbers of healthcare facilities within the geographic locations of interest.

20. The computer program product of claim 17, wherein the computer readable program code instructions for execution by the processor further cause the processor to:

determine population profile data for a highest-ranked location of the ranked filtered remainder set of the geographic locations;

determine marketing information deployment costs for each of the mosquito activity abatement actions that are associated to the highest-ranked location as a function of the determined population profile data; and select a marketing campaign of the mosquito activity abatement actions that are associated to the highest-ranked location in response to determining that the selected marketing campaign best matches the determined population profile data at a deployment cost that meets a threshold associated with the exposure risk weighting and the population risk weighting values of the highest-ranked location.

* * * * *